United States Patent [19]

Brandman et al.

[11] 4,199,600

[45] Apr. 22, 1980

[54] PRESERVATION OF AQUEOUS SYSTEMS WITH α-HALO-β-AMINOCROTONIC ACID ESTERS

[75] Inventors: Harold A. Brandman, Glen Ridge; Milton Manowitz, Wayne; David L. Coffen, Glen Ridge, all of N.J.

[73] Assignees: Givaudan Corporation, Clifton; Hoffmann-La Roche Inc., Nutley, both of N.J.

[21] Appl. No.: 934,294

[22] Filed: Aug. 17, 1978

[51] Int. Cl.$^2$ .............................................. A61K 31/22
[52] U.S. Cl. .................................................. 424/314
[58] Field of Search ........................... 424/314; 210/62

[56] References Cited

U.S. PATENT DOCUMENTS 2,379,294  6/1945  Gooding .............................. 424/314

OTHER PUBLICATIONS

Chemical Abstracts 82: p31347 (1975).

*Primary Examiner*—Frederick E. Waddell
*Attorney, Agent, or Firm*—Robert F. Tavares; Thomas Cifelli, Jr.

[57] ABSTRACT

Methods and compositions for inhibiting or preventing the growth of microorganisms in aqueous systems wherein the growth is inhibited or prevented by the presence of an effective amount of an α-halo-β-aminocrotonic acid ester.

11 Claims, No Drawings

PRESERVATION OF AQUEOUS SYSTEMS WITH α-HALO-β-AMINOCROTONIC ACID ESTERS

THE INVENTION

A number of aqueous systems are susceptible to antimicrobial growth. Among these are cosmetics, latex paints, polymer emulsions, oil in water emulsions used in industry (e.g., metal working fluids, textile lubricants, etc.), adhesives, water used in industrial cooling towers, white water in the paper mills and the like. The growth of bacteria and fungi in such systems can be a serious problem if not properly controlled. For example, industrial aqueous systems are susceptible to slime formation which, if unchecked, can cause severe maintenance and production problems. Similarly, consumer products such as cosmetics can be damaged by the growth of bacteria, fungi or algae.

There is, consequently, a continuing need to provide effective and economical antimicrobial agents which protect these systems. The finding of this invention is that compositions and methods utilizing α-halo-β-aminocrotonic acid esters provide effective control of such microbial growth. These esters are effective against a broad spectrum of bacteria including gram positive bacteria, gram negative bacteria and molds. The breadth of their activity is illustrated in the examples.

The α-halo-β-aminocrotonic acid esters may be prepared from the corresponding β-aminocrotonic acid esters by reacting them with the appropriate hypohalite.

DESCRIPTION OF THE PREFERRED EMBODIMENTS

The α-halo-β-aminocrotonic acid esters may be added to the aqueous systems or formulations undiluted or dissolved in organic solvents such as alcohols, acetone, dimethylformamide and the like. They may be added alone or in combination with other biocides and/or functional compounds such as antioxidants, anticorrosive agents, surfactants, etc.

Concentrations from below 0.005 to above 0.3% are effective. Use of larger concentrations, while feasible, is recommended only for unusual applications. It is preferred to use concentrations from about 0.01% to about 0.2%.

The α-halo-β-aminocrotonic acid esters can be used as preservatives for oil in water emulsions such as metal working fluids, textile lubricants and the like. A number of oil in water emulsions are used in industry, for example in the high speed metal working and textile industries, for their cooling, lubricating, antistatic and anticorrosive properties. Unless adequately protected by an effective preservative, such systems are susceptible to bacterial decomposition producing obnoxious odors and potential health hazards. [Detailed descriptions of these systems, their microbiological problems and difficulties in their preservation can be found in: Bennet, E. O., Soap Chem. Specialties, 32, 46 (1956). Fabian, F. W. & Pivnick, H., Applied Microbiology, 1 (1953)].

In practicing the invention, the α-halo-β-aminocrotonic acid esters may be added directly by dissolving in the oil portion which is later mixed with water to form the water oil emulsion. Alternatively it may be added to the final emulsion either undiluted or dissolved in a solvent such as dimethylformanide, alcohol, acetone, etc. Similar methods known in the art for adding preservatives to such water and oil emulsions may also be used.

There can be used as little as about 0.005%. Although amounts greater than 0.3% are operable, they are recommended only for unusual applications. It is preferred to use amounts in the range of from about 0.01% to about 0.20%, with amounts in the range of about 0.02% to 0.10% being especailly preferred.

The α-halo-β-aminocrotonic acid esters are particularly effective as cosmetic preservatives [Problems encountered in the preservation of cosmetics are described by Dunnigan, A. P., Drug and Cosmetic Industries, 103, 43, (1968)].

The compounds may be added to the finished cosmetic product directly or dissolved in suitable solvents such as alcohol, acetone, dimethyl formamide, etc. Alternatively the compounds may be dissolved in the oils or other raw materials used in the formula and then formulated in the final product.

In cosmetic preparations, concentrations as low as 0.01% are found to be operable. Concentrations greater than 0.30%, while operable, are recommended only for unusual applications. Concentrations in the range of from about 0.01% to about 0.20% are preferred with concentrations of about 0.05% to 0.10% being especially preferred.

The α-halo-β-aminocrotonic acid esters are particularly effective as slimicides. For example it can be used to protect so-called white water systems utilized in paper manufacture from the formation of slimes and the like which are known to affect these systems.

In controlling slime formation, concentrations as low as 0.005% are found to be operable. Concentrations greater than 0.20%, while operable, are recommended only for unusual applications. Concentrations in the range of from about 0.010% to about 0.10% are preferred with concentrations of about 0.02% to about 0.05% being especially preferred.

While the compound is effective when added directly, it is preferred to add it dissolved in a suitable solvent such as diethylene glycol, dipropylene glycol in polethylene glycol and the like. Other methods known in the art for adding preservatives to such aqueous systems may also be used.

ILLUSTRATION OF PREFERRED EMBODIMENTS

A number of examples are provided herein to illustrate the preferred embodiments of this invention. The examples provided are included for the sole purpose of illustrating the preferred embodiments and should not be construed as limiting. They are intended to embrace any equivalents or obvious extensions which are known or should be known to a person skilled in the art.

It is preferred to use the lower α-chloro-β-aminocrotonic acid esters, e.g., the methyl through butyl esters since these are more easily obtainable. It is especially preferred to use the methyl and ethyl esters.

In each of the examples below the utility is illustrated using the α-chloro-β-aminocrotonic acid methyl ester.

EXAMPLE I

General Antimicrobial Activity

The α-halo-β-aminocrotonic acid esters are active against a wide variety of microorganisms as illustrated below:

A 6% soltuion of α-halo-β-aminocrotonic acid ester in dimethyl formamide was prepared. The 6% solution was then 5-fold serially diluted in test tubes to give the desired concentrations when mixed with agar and poured into sterile Petri dishes. For instance, 0.8 ml of a 6% stock solution plus 24.2 ml of agar gives a test concentration of 1920 mcg/ml, the highest level tested. Tryptone glucose extract agar is used for the bacterial testing; mildew glucose agar for the fungal testing. The bacterial plates were spot inoculated with 24-hour nutrient broth cultures and incubated at 37° C. for 48 hours. The fungal plates were spot inoculated with spore suspensions and incubated at 28° C. for seven days. At the end of the incubation periods, all plates were examined for growth. The minimum inhibitory concentration (MIC) for each organism is expressed in Table I. In the ranges presented, growth is observed only at the lower concentration.

TABLE I

| | Minimum Inhibitory Concentration[a] | |
|---|---|---|
| Bacteria | | |
| Staphylococcus aureus | 76.8 mcg/ml | 384 mcg/ml |
| Escherichia coli | 76.8 mcg/ml | 384 mcg/ml |
| Pseudomonas aeruginosa | 76.8 mcg/ml | 384 mcg/ml |
| Proteus vulgaris | 15.8 mcg/ml | 76.8 mcg/ml |
| Bacillus subtilis | 76.8 mcg/ml | 384 mcg/ml |
| Fungi | | |
| Aspergillus niger | 15 mcg/ml | 76 mcg/ml |
| Aspergillis oryzae | 15 mcg/ml | mcg/ml |
| Pencillium piscarium | 76 mcg/ml | 384 mcg/ml |
| Aureobasidium pullulans | 15 mcg/ml | 76 mcg/ml |

[a] For α-chloro-β-aminocrotonic acid methyl ester

EXAMPLE II

Utility as a Cosmetic Preservative

The α-halo-β-aminocrotonic acid esters are effective cosmetic preservatives. Two-fold serial dilutions of 6% solutions of the α-halo-β-aminocrotonic acid esters in dimethylformamide were added to a cosmetic lotion of the following formulation:

| | |
|---|---|
| Stearic acid | 1.4 g |
| Mineral Oil | 2.3 g |
| Arlacel 60 (Sorbitan monostearate) | 0.7 g |
| Tween 20 [Polyoxyethylene (20) sorbitan monostearate] | 1.6 g |
| Distilled water | 94.0 g |

The lotions were inoculated with both *Pseudomonas aeruginosa* and *Aspergillus niger* and incubated at 28° C. At weekly intervals, the lotions were examined for microorganisms by conventional streak-plate methods or by macroscopic observation. The lotions were then reinoculated with the test organisms and reincubated. Table II shows the minimum inhibitory concentration that was effective in preventing microbial growth for the four week period.

TABLE II

| | Minimum Inhibitory Concentration Range[a] (micrograms/milliliter) | |
|---|---|---|
| Week | Pseudomonas aeruginosa | Aspergillus niger |
| 1 | <125 mcg/ml | <125 mcg/ml |
| 2 | <125 mcg/ml | <125 mgl/ml |
| 3 | <125 mcg/ml | 1,000–2,000 mcg/ml |

TABLE II-continued

| | Minimum Inhibitory Concentration Range[a] (micrograms/milliliter) | |
|---|---|---|
| Week | Pseudomonas aeruginosa | Aspergillus niger |
| 4 | <125 mcg/ml | >2,000 mcg/ml |

[a] α-Chloro-β-aminocrotonic acid methyl ester.

EXAMPLE III

The utility of α-halo-β-aminocrotonic acid esters in water and oil emulsions is illustrated below using a commercially available cutting oil and a commercially available textile lubricant.

A. Utility as a Cutting Oil Preservative

The α-chloro-β-aminocrotonic acid methyl ester is an effective cutting preservative. The data of Table III clearly illustrate its effectiveness.

In running these tests, two-fold serial dilutions of 6% solutions of the compound in dimethylformamide was added to 3.3% cutting oil elumsions. The emulsions were prepared by diluting with water a commercially available cutting oil concentrate. The emulsions were inoculated with a culture of *Pseudomonas aeruginosa* and incubated at 28° C. on a rotary shaker. At weekly intervals, the emulsions were examined for bacteria by conventional streakplate methods. The emulsions were then reinoculated with *Pseudomonas aeruginosa* and reincubated.

TABLE III-A

| | Minimum Inhibitory Concentration Range[a] (micrograms/milliliter) |
|---|---|
| Week | Psuedomonas aeruginosa |
| 1 | <31.3 mcg/ml |
| 2 | 62.5–125 mcg/ml |
| 3 | 125–250 mcg/ml |
| 4 | 250–500 mcg/ml |

B. Utility as a Textile Lubricant Preservative

The test run was the same as for the cutting oil above except that a commercial textile lubricant was substituted.

TABLE III-B

| | Minimum Inhibitory Concentration Range[a] (micrograms/milliliter) |
|---|---|
| Week | Psuedomonas aeruginosa |
| 1 | 62.5–125 mcg/ml |
| 2 | 62.5–125 mcg/ml |
| 3 | 62.5–125 mcg/ml |
| 4 | 125–250 mcg/ml |

[a] α-Chloro-β-aminocrotonic acid methyl ester.

EXAMPLE IV

The utility of the α-halo-β-aminocrotonic acid esters as a slimicide for pulp and paper mill water systems was demonstrated by the following study.

Various quantities of a 6% solution of this compound in dimethylformamide were incorporated into 24 ml of a test substrate composed as follows:

8.4 g—Whatman No. 2 powdered cellulose
2.6 g—Sodium nitrate
1.0 g—Calcium sulfate
6.5 g—Maltose
1.0 g—Nutrient Broth, Difco
10.0 ml—Mersize Rm 70R (Monsanto)

2.5 ml—2% Alum
990 ml—Distilled water

The samples were inoculated with four different organisms and incubated at 28° C. At weekly intervals the samples were examined for the presence of microbial growth and reinoculated during a total incubation period of four weeks. The results, as tabulated in Table IV, show that α-chloro-β-aminocrotonic acid methyl ester is effective as a slimicide at a concentration of less than 62.5 mcg/ml.

TABLE IV

Effectiveness of α-Chloro-β-aminocrotonic acid methyl ester as a Slimicide. (mcg/ml)

| Organism | Weeks | | | |
|---|---|---|---|---|
|  | 1 | 2 | 3 | |
| P. aeruginosa | <62.5 | <62.5 | <62.5 | <62.5 |
| E. aerogenes | <62.5 | 125–250 | 250–500 | 250–500 |
| A. niger | <62.5 | <62.5 | <62.5 | <62.5 |
| P. Piscarium | <62.5 | <62.5 | <62.5 | 62.5–125 |

EXAMPLE V

The α-halo-β-aminocrotonic acid esters were prepared, as illustrated below, by reacting the corresponding β-aminocrotonic acid esters with the appropriate hypohalite.

α-Chloro-β-aminocrotonic acid methyl ester

A rapidly stirred mixture of methyl 3-aminocrotonate (5.0 g) water (50 ml), and methylene chloride (50 ml) was cooled in an ice bath and treated with aq. sodium hypochlorite (Clorox, 62 ml) by dropwise addition. Stirring was continued for 2 hours after which the layers were separated. The aqueous phase was extracted twice with methylene chloride. The methylene chloride solutions were combined and dried with sodium sulfate. Evaporation of the solvent gave 5.1 g (78.5%) of colorless crystals. An analytical sample recrystallized from cyclohexane had mp 68–70°; ir (Nujol) 3450, 3350, 1630, 1530 cm$^{-1}$; nmr 2.15 (s, 3H), 3.75 (s, 3H); mass spectrum m/e 118 (100%) and 149 (M+).

Anal. Calcd for $C_5H_8ClNO_2$: C, 40.15; H, 5.39; Cl, 23.70; N, 9.36. Found: C, 40.29; H, 5.44; Cl, 23.50; N, 9.30.

We claim:

1. A method of inhibiting or preventing the growth of bacteria and fungi in an aqueous composition subject to spoilage thereby which comprises incorporating in said composition an effective amount of a methyl, ethyl, propyl or butyl ester of α-chloro-β-aminocrotonic acid.

2. The method of claim 1 wherein the α-chloro-β-aminocrotonic acid ethyl ester is used.

3. The method of claim 1 wherein the α-chloro-β-aminocrotonic acid methyl ester is used.

4. A method according to claims 2 or 3 wherein the esters are utilized at a level of from about 0.01% to about 0.2%.

5. The method according to claims 2 or 3 wherein the composition to be protected is a cosmetic formulation.

6. The method according to claims 2 or 3 wherein the composition to be protected is a water and oil emulsion.

7. The method according to claims 2 or 3 wherein the composition to be protected is a cutting oil.

8. The method according to claims 2 or 3 wherein the composition to be protected is a textile lubricant.

9. The method according to claims 2 or 3 wherein the composition to be protected is a pulp and paper mill water system.

10. A cosmetic composition comprising an amount of α-chloro-β-aminocrotonic acid methyl or ethyl ester effective to inhibit or prevent spoilage.

11. An oil and water emulsion comprising an amount of α-chloro-β-aminocrotonic acid methyl or ethyl ester effective to inhibit or prevent the growth of bacteria and fungi.

* * * * *